(12) United States Patent
Mistretta

(10) Patent No.: US 7,865,227 B2
(45) Date of Patent: *Jan. 4, 2011

(54) IMAGE RECONSTRUCTION METHOD FOR CARDIAC GATED MAGNETIC RESONANCE IMAGING

(75) Inventor: Charles A. Mistretta, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 880 days.

This patent is subject to a terminal disclaimer.

(21) Appl. No.: 11/524,750

(22) Filed: Sep. 21, 2006

(65) Prior Publication Data

US 2007/0106149 A1  May 10, 2007

Related U.S. Application Data

(60) Provisional application No. 60/719,445, filed on Sep. 22, 2005, provisional application No. 60/738,444, filed on Nov. 21, 2005.

(51) Int. Cl.
*A61B 5/05* (2006.01)
*G06K 9/00* (2006.01)

(52) U.S. Cl. .................... 600/413; 600/428; 382/128; 382/131

(58) Field of Classification Search .............. None
See application file for complete search history.

(56) References Cited

U.S. PATENT DOCUMENTS

| | | | |
|---|---|---|---|
| 4,982,328 A * | 1/1991 | Kasugai | 600/410 |
| 5,502,385 A | 3/1996 | Kuhn et al. | |
| 5,603,322 A | 2/1997 | Jesmanowicz et al. | |
| 5,604,778 A | 2/1997 | Polacin et al. | |
| 5,933,006 A | 8/1999 | Rasche et al. | |
| 5,987,347 A * | 11/1999 | Khoury et al. | 600/410 |
| 6,487,435 B2 * | 11/2002 | Mistretta et al. | 600/420 |
| 6,490,472 B1 | 12/2002 | Li et al. | |
| 6,807,248 B2 | 10/2004 | Mihara et al. | |
| 6,954,067 B2 | 10/2005 | Mistretta | |

(Continued)

FOREIGN PATENT DOCUMENTS

EP  0 627 633 A1  7/1994

(Continued)

OTHER PUBLICATIONS

Wieslaw, L. Nowinski, The Iterated Normalized Backprojection Method of Image Reconstruction, Institute of Computer Science, Polish Academy of Sciences Ordona 21, 01-237 Warsaw, Poland.

(Continued)

*Primary Examiner*—Long V. Le
*Assistant Examiner*—Angela M Hoffa
(74) *Attorney, Agent, or Firm*—Quarles & Brady LLP

(57) ABSTRACT

A cardiac gated acquisition of MR data during a breath-hold employs a hybrid PR pulse sequence to acquire projection views from which image frames may be reconstructed at a plurality of cardiac phases during each heartbeat. Composite images are reconstructed at each cardiac phase using interleaved projection views acquired during all the heartbeats. The composite images are used to reconstruct the highly undersampled image frames at the same cardiac phase using a highly constrained backprojection method.

30 Claims, 16 Drawing Sheets

U.S. PATENT DOCUMENTS

| | | | |
|---|---|---|---|
| 7,358,730 B2* | 4/2008 | Mistretta et al. | 324/307 |
| 7,408,347 B2* | 8/2008 | Mistretta et al. | 324/307 |
| 7,519,412 B2* | 4/2009 | Mistretta | 600/407 |
| 7,545,901 B2* | 6/2009 | Mistretta | 378/4 |
| 7,647,088 B2* | 1/2010 | Mistretta et al. | 600/428 |
| 7,711,166 B2* | 5/2010 | Mistretta et al. | 382/128 |
| 2001/0027262 A1 | 10/2001 | Mistretta et al. | |
| 2005/0251023 A1* | 11/2005 | Kannengiesser et al. | 600/410 |
| 2005/0261574 A1* | 11/2005 | Li et al. | 600/420 |
| 2005/0272997 A1* | 12/2005 | Grist et al. | 600/410 |
| 2006/0079754 A1* | 4/2006 | Welch et al. | 600/410 |
| 2007/0038073 A1* | 2/2007 | Mistretta | 600/410 |
| 2007/0156044 A1* | 7/2007 | Mistretta et al. | 600/410 |
| 2007/0167707 A1* | 7/2007 | Mistretta et al. | 600/407 |
| 2007/0167728 A1* | 7/2007 | Mistretta et al. | 600/410 |
| 2008/0219535 A1* | 9/2008 | Mistretta et al. | 382/131 |

FOREIGN PATENT DOCUMENTS

| | | |
|---|---|---|
| WO | WO 2005/026765 | 3/2005 |
| WO | WO 2005/069031 | 7/2005 |

OTHER PUBLICATIONS

Y. Huang et al, Time-Resolved 3D MR Angiography by Interleaved Biplane Projection, Proc. Intl. Soc. Mag. Reson. Med. 13 (2005).

T.A. Cashen et al, Comparison of Temporal and Spatial Undersampling Techniques for Time-Resolved Contrast-Enhanced MR Angiography, Proc. Intl. Soc. Mag. Reson. Med. 13, (2005).

Graeme C. McKinnon et al, Towards Imaging the Beating Heart Usefully with a Conventional CT Scanner, Trans. on Biomedical Eng., vol. BME-28, No. 2, pp. 123-127, Feb. 1981.

Kathryn L. Garden et al, 3-D Reconstruction of the Heart from few Projections: A Practical Implementation of the McKinnon-Bates Algorithm, Trans. on Biomedical Eng., vol. MI-5, No. 4, pp. 233-234, Dec. 1986.

A.L. Wentland et al, Technique for Acquiring MR Images of CSF Flow During a Valsalva Maneuver, Med. Phys. Univ. of WI, Madison WI.

K.M. Johnson et al, Average and Time-Resolved Dual Velocity Encoded Phase Contrast Vastly Undersampled Isotropic Projection Imaging, Med. Phys. Univ. of WI, Madison WI.

K.M. Johnson et al, Transtenotic Pressure Gradient Measurements Using Phase Contrast Vastly Undersampled Isotropic Projection Imaging (PC-VIPR) in a Cabin Model, Med. Phys. Univ. of WI, Madison WI.

C.A. Mistretta et al, Highly Constrained Backprojection for Time-Resolved MRI, Mag. Reson. Med. 55:30-40 (2006).

Zhi-Pei Liang et al, Constrained Reconstruction Methods in MR Imaging, Reviews of Mag. Reson. in Med. vol. 4, pp. 67-185, 1992.

J.G. Pipe et al, Spiral Projection Imaging: a new fast 3D trajectory, Proc. Intl. Soc. Mag. Reson. Med. 13, (2005).

K.V. Koladia et al, Rapid 3D PC-MRA using Spiral Projection Imaging, Proc. Intl. Soc. Mag. Reson. Med. 13, (2005).

J.Tsao et al, k-t BLAST and k-t SENSE: Dynamic MRI With High Frame Rate Exploiting Spatiotemporal Correlations, Mag. Reson. Med. 50:1031-1042 (2003).

Zhi-Pei Liang et al, Constrained Imaging-Overcoming the Limitations of the Fourier Series, IEEE Engineering in Medicine and Biology, Sep./Oct. 1996, pp. 126-132.

Zhi-Pei Liang et al, Fast Algorithm for GS-Model-Based Image Reconstruction in Data-Sharing Fourier Imaging, IEEE Transactions on Med. Imaging, vol. 22, No. 8, pp. 1026-1030, Aug. 2003.

Klass P. Pruessmann et al, Advances in Sensitivity Encoding With Arbitrary k-Space Trajectories, Mag. Reson. in Med. 46:638-651 (2001).

R. Fahrig et al, Use of a C-Arm System to Generate True Three-dimensional Computed Rotational Angiograms: Preliminary In Vitro and In Vivo Results, AJNR: 18, pp. 1507-1514, Sep. 1997.

A.V. Barger, et al, Single Breath-Hold 3D Contrast-Enhanced Method for Assessment of Cardiac Function, Mag. Reson. in Med. 44:821-824 (2000).

J. Du et al, Time-Resolved Undersampled Projection Reconstruction Imaging for High-Resolution CE-MRA of the Distal Runoff Vessels, Mag. Reson. in Med. 48:516-522 (2002).

Ashwani Aggarwal et al, Imaging in Turbid Media by Modified Filtered Back Projection Method Using Data From Monte Carlo Simulation, Proc. of SPIE vol. 5047, pp. 314-324.

Xavier Golay, et al, PRESTO-SENSE: An Ultrafast Whole-Brain fMRI Technique, Mag. Reson. in Med. 43:779-786 (2000).

Ronald R. Price, et al, Practical Aspects of Functional MRI (NMR Task Group #6), Medical Physics, vol. 29, No. 8, pp. 1892-1912, Aug. 2002.

M.S. Hansen et al, k-t Blast Reconstruction From Arbitrary k-t space Sampling: Application to Dynamic Radial Imaging, Proc. Intl. Soc. Mag. Reson. Med. 13 p. 684 (2005).

* cited by examiner

IMAGE RECONSTRUCTION METHOD FOR CARDIAC GATED MAGNETIC RESONANCE IMAGING

CROSS-REFERENCE TO RELATED APPLICATIONS

This application is based on U.S. Provisional Patent Application Ser. No. 60/719,445 filed on Sep. 22, 2005 and entitled "HIGHLY CONSTRAINED IMAGE RECONSTRUCTION METHOD"; and Ser. No. 60/738,444 filed on Nov. 21, 2005 and entitled "IMAGE RECONSTRUCTION METHOD FOR CARDIAC GATED MAGNETIC RESONANCE IMAGING."

BACKGROUND OF THE INVENTION

The field of the invention is nuclear magnetic resonance imaging methods and systems. More particularly, the invention relates to the reconstruction of images from cardiac gated magnetic resonance acquisitions.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, Mz, may be rotated, or "tipped", into the x-y plane to produce a net transverse magnetic moment Mt. A signal is emitted by the excited spins after the excitation signal $B_1$, is terminated, this signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. Each measurement is referred to in the art as a "view" and the number of views determines the resolution of the image. The resulting set of received NMR signals, or views, or k-space samples, are digitized and processed to reconstruct the image using one of many well known reconstruction techniques. The total scan time is determined in part by the number of measurement cycles, or views, that are acquired for an image, and therefore, scan time can be reduced at the expense of image resolution by reducing the number of acquired views.

The most prevalent method for acquiring an NMR data set from which an image can be reconstructed is referred to as the "Fourier transform" imaging technique or "spin-warp" technique. This technique is discussed in an article entitled "Spin-Warp NMR Imaging and Applications to Human Whole-Body Imaging", by W. A. Edelstein et al., *Physics in Medicine and Biology*, Vol. 25, p. 751-756 (1980). It employs a variable amplitude phase encoding magnetic field gradient pulse prior to the acquisition of NMR signals to phase encode spatial information in the direction of this gradient. In a two-dimensional implementation (2DFT), for example, spatial information is encoded in one direction by applying a phase encoding gradient ($G_y$) along that direction, and then a signal is acquired in the presence of a readout magnetic field gradient ($G_x$) in a direction orthogonal to the phase encoding direction. The readout gradient present during the spin-echo acquisition encodes spatial information in the orthogonal direction. In a typical 2DFT pulse sequence, the magnitude of the phase encoding gradient pulse $G_y$ is incremented ($G_y$) in the sequence of views that are acquired during the scan. In a three-dimensional implementation (3DFT) a third gradient ($G_z$) is applied before each signal readout to phase encode along the third axis. The magnitude of this second phase encoding gradient pulse $G_z$ is also stepped through values during the scan. These 2DFT and 3DFT methods sample k-space in a rectilinear pattern as shown in FIG. 2 and the k-space samples lie on a Cartesian grid.

Magnetic resonance angiography (MRA) uses the magnetic resonance phenomenon to produce images of the human vasculature and heart. To enhance the diagnostic capability of MRA a contrast agent such as gadolinium can be injected into the patient prior to the MRA scan. As described in U.S. Pat. No. 5,417,213 the trick with this contrast enhanced (CE) MRA method is to acquire the central k-space views at the moment the bolus of contrast agent is flowing through the vasculature of interest. Collection of the central lines of k-space during peak arterial enhancement is key to the success of a CEMRA exam. If the central lines of k-space are acquired prior to the arrival of contrast, severe image artifacts can limit the diagnostic information in the image. Alternatively, arterial images acquired after the passage of the peak arterial contrast are sometimes obscured by the enhancement of veins. In many anatomic regions, such as the carotid or renal arteries, the separation between arterial and venous enhancement can be as short as 6 seconds.

The acquisition of MRA data is timed such that the central region of k-space is acquired as the bolus of contrast agent arrives in the arteries of interest. The ability to time the arrival of contrast varies considerably and it is helpful in many applications to acquire a series of MRA images in a dynamic study which depicts the separate enhancement of arteries and veins. A temporal series of images is also useful for observing delayed vessel filling patterns caused by disease. This requirement has been partially addressed by acquiring a series of time resolved images using a 3D "Fourier" acquisition as described by Korosec F., Frayne R, Grist T., Mistretta C., "Time-Resolved Contrast-Enhanced 3D MR Angiography", *Magn. Reson. Med.* 1996; 36:345-351 and in U.S. Pat. No. 5,713,358.

More recently projection reconstruction methods have been used for acquiring time-resolved MRA data as disclosed in U.S. Pat. No. 6,487,435. Projection reconstruction methods, sometimes referred to as "radial" acquisitions, have been known since the inception of magnetic resonance imaging. Rather than sampling k-space in a rectilinear scan pattern as is done in Fourier imaging and shown in FIG. 2, projection reconstruction methods acquire a series of views that sample radial lines extending outward from the center of k-space as shown in FIG. 3. The number of views needed to sample k-space determines the length of the scan and if an insufficient number of views are acquired, streak artifacts are produced in the reconstructed image. The technique disclosed in U.S. Pat. No. 6,487,435 reduces such streaking by acquiring successive undersampled images with interleaved views and sharing peripheral k-space data between successive images.

There are two methods used to reconstruct images from an acquired set of k-space projection views as described, for example, in U.S. Pat. No. 6,710,686. The most common method is to regrid the k-space samples from their locations on the radial sampling trajectories to a Cartesian grid. The image is then reconstructed by performing a 2D or 3D Fourier transformation of the regridded k-space samples. The second method for reconstructing an image is to transform the radial k-space projection views to Radon space by Fourier transforming each projection view. An image is reconstructed from these signal projections by filtering and backprojecting them into the field of view (FOV). As is well known in the art, if the acquired signal projections are insufficient in number to satisfy the Nyquist sampling theorem, streak artifacts are produced in the reconstructed image.

The standard backprojection method is illustrated in FIG. 4. Each acquired signal projection profile 10 is backprojected onto the field of view 12 by projecting each signal sample 14 in the profile 10 through the FOV 12 along the projection path as indicted by arrows 16. In backprojecting each signal sample 14 in the FOV 12 we have no a priori knowledge of the subject and the assumption is made that the NMR signals in the FOV 12 are homogeneous and that the signal sample 14 should be distributed equally in each pixel through which the projection path passes. For example, a projection path 18 is illustrated in FIG. 4 for a single signal sample 14 in one signal projection profile 10 as it passes through N pixels in the FOV 12. The signal value (P) of this signal sample 14 is divided up equally between these N pixels:

$$S_n = (P \times 1)/N \tag{1}$$

where: $S_n$ is the NMR signal value distributed to the $n^{th}$ pixel in a projection path having N pixels.

Clearly, the assumption that the NMR signal in the FOV 12 is homogeneous is not correct. However, as is well known in the art, if certain filtering corrections are made to each signal profile 10 and a sufficient number of filtered profiles are acquired at a corresponding number of projection angles, the errors caused by this faulty assumption are minimized and image artifacts are suppressed. In a typical, filtered backprojection method of image reconstruction, 400 projections are required for a 256×256 pixel 2D image and 203,000 projections are required for a 256×256×256 voxel 3D image. If the method described in the above-cited U.S. Pat. No. 6,487,435 is employed, the number of projection views needed for these same images can be reduced to 100 (2D) and 2000 (3D).

When imaging certain arteries, such as coronary arteries, the motion of the beating heart becomes an issue. To reduce motion artifacts in MRI or MRA images it is common practice to cardiac gate the acquisition of views using an ECG signal indicative of cardiac phase. As described, for example, in U.S. Pat. No. 5,329,925 a group, or segment, of views are acquired at each of one or more cardiac phases during each cardiac cycle. For example, 8 different views may be acquired at a particular cardiac phase and after 16 heart beats a total of 8×16=128 different views are acquired from which an image may be reconstructed. Since a single breath-hold is typically 16-20 heartbeats it is highly desirable to acquire all the data within breath-hold in order to avoid artifacts due to respiratory motion.

While a decent single-slice, 2D image may be acquired at one or more cardiac phases during a single breath-hold using projection reconstruction methods and view sharing, prior methods are not fast enough to acquire a 3D image or multiple 2D slices at each cardiac phase. Such images are necessary when the subject of the examination does not lie in a single 2D plane (e.g., coronary arteries) and either a multi-slice or 3D image acquisition is needed.

SUMMARY OF THE INVENTION

The present invention is a new method for producing cardiac gated MR images and particularly a method for improving the quality of highly undersampled images acquired at specific cardiac phases. A series of undersampled image frames are acquired at a selected cardiac phase during successive heart beats. The views acquired during successive heart beats sample interleaved trajectories in k-space and these are combined and used to reconstruct a composite image that depicts the subject at the selected cardiac phase. This composite image is used in a highly constrained backprojection of each projection view by weighting the distribution of back projected signal samples.

A discovery of the present invention is that good quality frame images can be produced with far fewer acquired views if a priori knowledge of the NMR signal contour in the FOV 12 is used in the backprojection image reconstruction process instead of the assumed homogeneous signal contour. Referring to FIG. 5, for example, the signal contour in the FOV 12 may be known to include structures such as blood vessels 18 and 20. That being the case, when the backprojection path 8 passes through these structures a more accurate distribution of the signal sample 14 in each pixel is achieved by weighting the distribution as a function of the known NMR signal contour at that pixel location. As a result, a majority of the signal sample 14 will be distributed at the pixels that intersect the structures 18 and 20. For a backprojection path 8 having N pixels this may be expressed as follows:

$$S_n = (P \times C_n) \bigg/ \sum_{n=1}^{N} C_n \tag{2}$$

where: P=the NMR signal sample value; and
Cn=signal value of the composite image at the nth pixel along the backprojection path.

The numerator in equation (2) weights each pixel using the corresponding NMR signal value in the composite image and the denominator normalizes the value so that all back-projected signal samples reflect the projection sums for the image frame and are not multiplied by the sum of the composite image. It should be noted that while the normalization can be performed on each pixel separately after the backprojection is performed, in many clinical applications it is far easier to normalize the projection P before the backprojection. In this case, the projection P is normalized by dividing it by the corresponding value Pc in a projection through the composite image at the same view angle. The normalized projections P/Pc are then backprojected and the resulting image is then multiplied by the composite image.

A 3D embodiment of the invention is shown graphically in FIG. 6 for a single 3D projection view characterized by the view angles θ and φ. This projection view is Fourier transformed to form a signal contour and it is back projected along axis 16 and spread into a Radon plane 21 at a distance r along the backprojection axis 16. Instead of a filtered back projection in which projection signal contour values are filtered and uniformly distributed into the successive Radon planes, along axis 16, the projection signal contour values are distributed in the Radon plane 21 using the information in the composite image. The composite image in FIG. 6 contains vessels 18 and 20. The weighted signal contour value is deposited at image location x, y, z in the Radon plane 21 based on the intensity at the corresponding location x, y, z in the composite image. This is a simple multiplication of the signal profile value by the corresponding composite image voxel value. This product is then normalized by dividing the product by the profile value from the corresponding image space profile formed from the composite image. The formula for the 3D reconstruction is $$I(x,y,z) = \Sigma(P(r;\theta,\phi) * C(x,y,z)_{(r;\theta,\phi)}/P_c(r;\theta,\phi) \tag{2a}$$

where the sum ($\Sigma$) is over all projections in the time frame and the x, y, z values in a particular Radon plane are calculated using the profile value $P(r,\theta,\phi)$ at the appropriate $r,\theta,\phi$ value for that plane. $P_c(r,\theta,\phi)$ is the corresponding profile value from the composite image and $C(x,y,z)_{r,\theta,\phi}$ is the composite image value at $(r,\theta,\phi)$ Another discovery of the present invention is that this image reconstruction method can be advantageously employed in a cardiac gated acquisition in which a series of undersampled frame images are acquired at the same cardiac phase. By interleaving the views of the successive image frame acquisitions, views from successive image frames can be combined and used to reconstruct a higher quality composite image. This composite image is then used in the above described backprojection reconstruction of each image frame.

Another aspect of the present invention is the reconstruction of image frames acquired during a cardiac gated scan with a 3D hybrid projection reconstruction pulse sequence. Projection views are acquired to sample k-space with radial trajectories in a 2D slice and phase encoding is employed to acquire multiple slices along an axial direction. A composite image is reconstructed for each of the multiple slice locations and these composite images are employed during the backprojection reconstruction of the 2D slices in each image frame.

DETAILED DESCRIPTION OF THE PREFERRED EMBODIMENT

Figure 1:
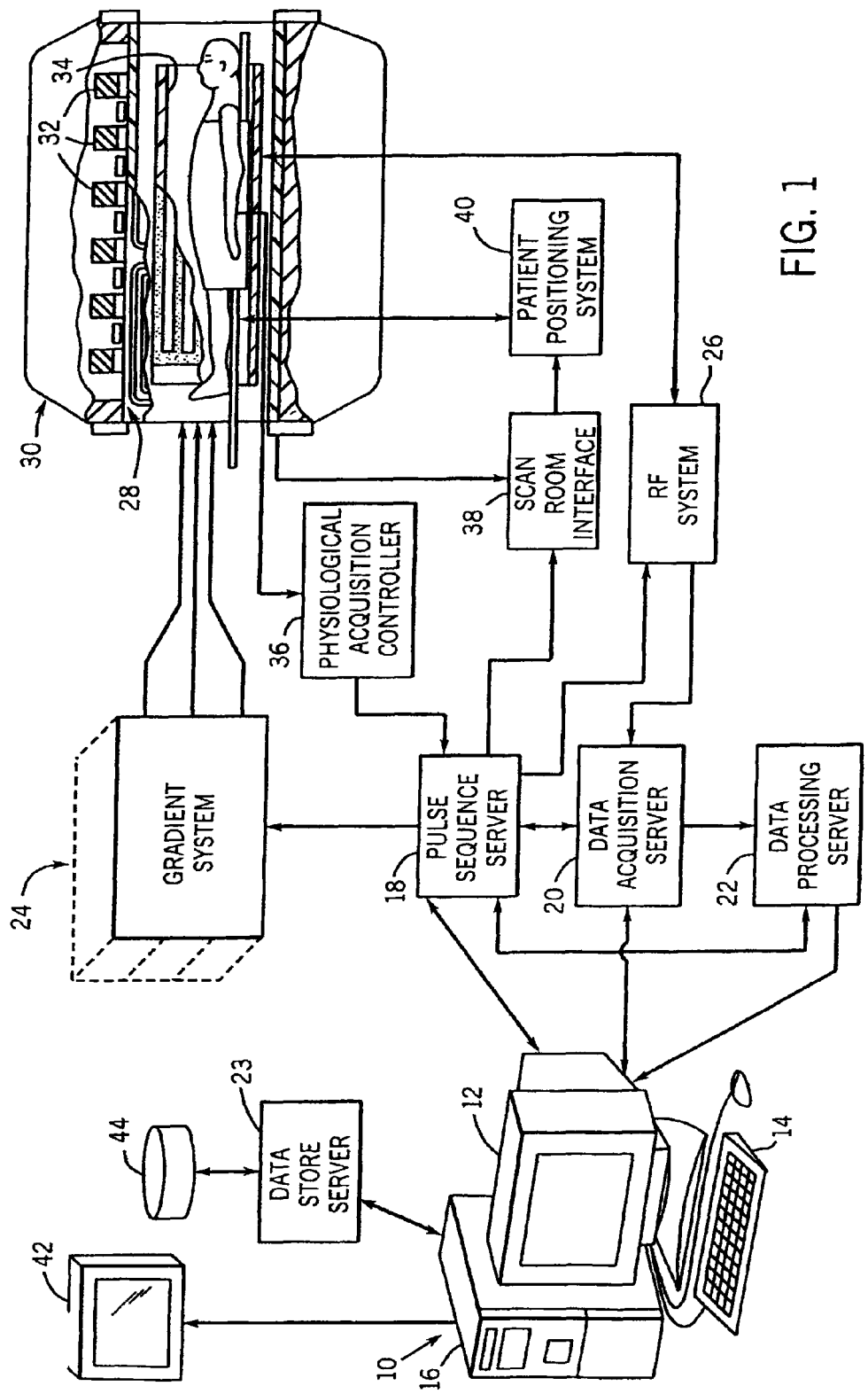
FIG. 1 is a block diagram of an MRI system which employs the present invention.
Figure 2:
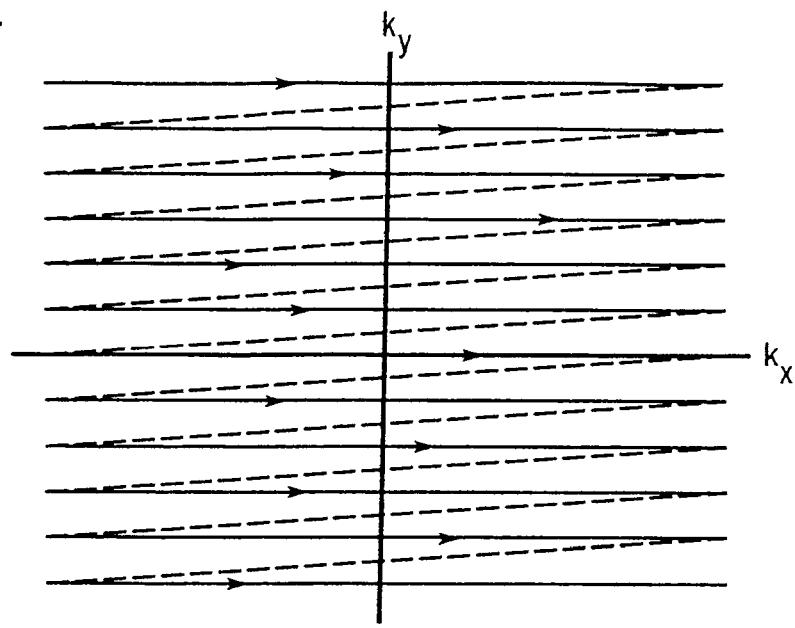
FIG. 2 is a pictorial representation of k-space sampling using a Fourier transform technique.
Figure 3:
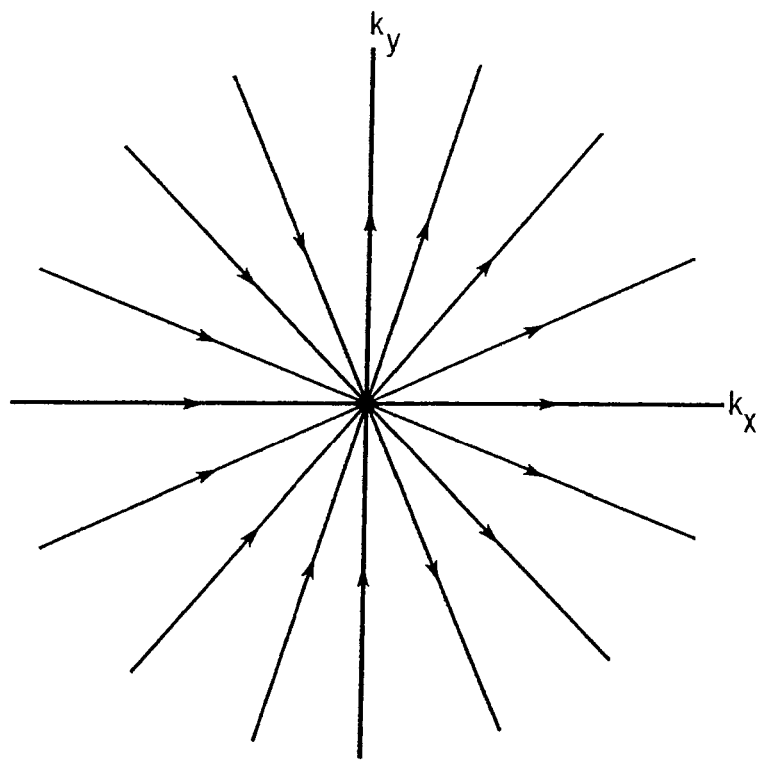
FIG. 3 is a pictorial representation of k-space sampling using a projection reconstruction technique.
Figure 4:
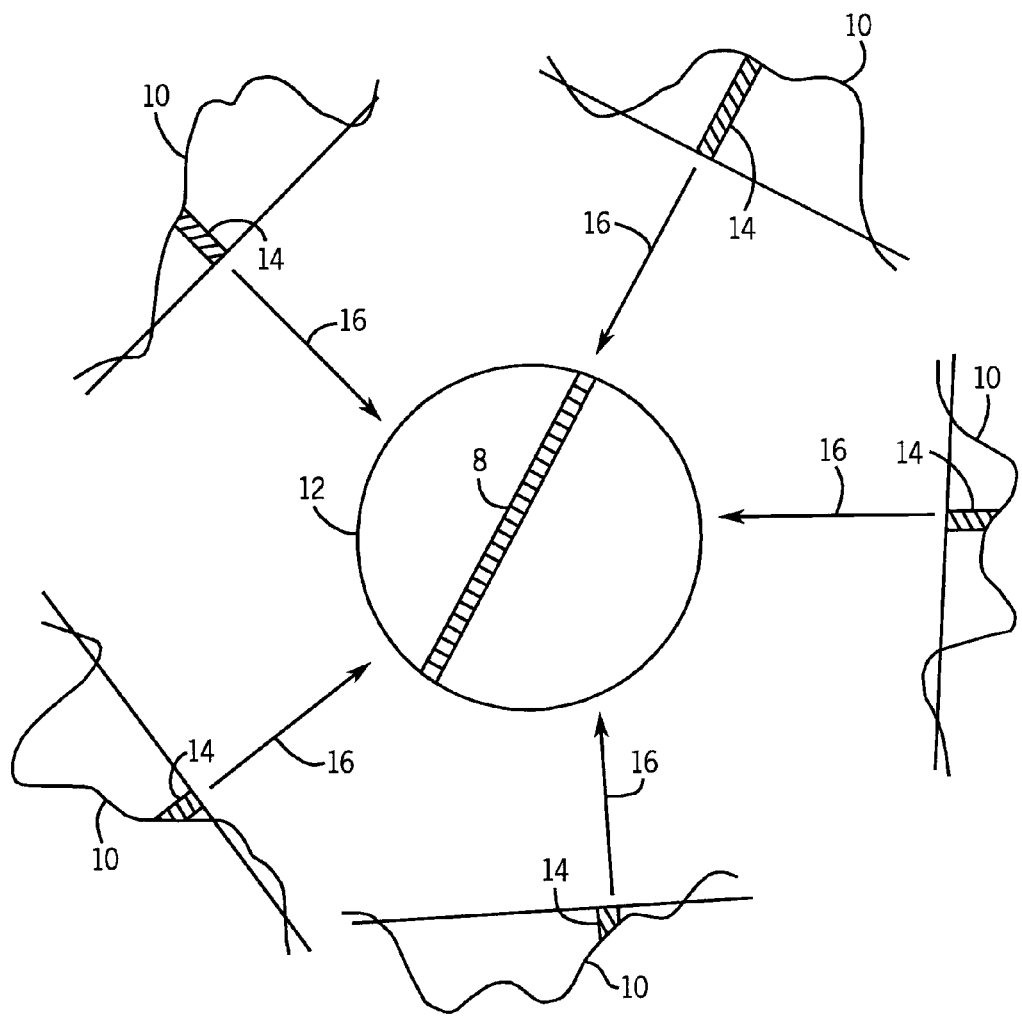
FIG. 4 is a pictorial representation of a conventional backprojection reconstruction method.

Referring particularly to FIG. 1, the preferred embodiment of the invention is employed in an MRI system. The MRI system includes a workstation 110 having a display 112 and a keyboard 114. The workstation 110 includes a processor 116 which is a commercially available programmable machine running a commercially available operating system. The workstation 110 provides the operator interface which enables scan prescriptions to be entered into the MRI system.

The workstation 110 is coupled to four servers: a pulse sequence server 118; a data acquisition server 120; a data processing server 122, and a data store server 23. In the preferred embodiment the data store server 23 is performed by the workstation processor 116 and associated disc drive interface circuitry. The remaining three servers 118, 120 and 122 are performed by separate processors mounted in a single enclosure and interconnected using a 64-bit backplane bus. The pulse sequence server 118 employs a commercially available microprocessor and a commercially available quad communication controller. The data acquisition server 120 and data processing server 122 both employ the same commercially available microprocessor and the data processing server 122 further includes one or more array processors based on commercially available parallel vector processors.

The workstation 10 and each processor for the servers 118, 120 and 122 are connected to a serial communications network. This serial network conveys data that is downloaded to the servers 118, 120 and 122 from the workstation 110 and it conveys tag data that is communicated between the servers and between the workstation and the servers. In addition, a high speed data link is provided between the data processing server 122 and the workstation 110 in order to convey image data to the data store server 23.

The pulse sequence server 118 functions in response to program elements downloaded from the workstation 110 to operate a gradient system 24 and an RF system 26. Gradient waveforms necessary to perform the prescribed scan are produced and applied to the gradient system 24 which excites gradient coils in an assembly 28 to produce the magnetic field gradients $G_x$, $G_y$ and $G_z$ used for position encoding NMR signals. The gradient coil assembly 28 forms part of a magnet assembly 30 which includes a polarizing magnet 32 and a whole-body RF coil 34.

RF excitation waveforms are applied to the RF coil 34 by the RF system 26 to perform the prescribed magnetic resonance pulse sequence. Responsive NMR signals detected by the RF coil 34 are received by the RF system 26, amplified, demodulated, filtered and digitized under direction of commands produced by the pulse sequence server 118. The RF system 26 includes an RF transmitter for producing a wide variety of RF pulses used in MR pulse sequences. The RF transmitter is responsive to the scan prescription and direction from the pulse sequence server 118 to produce RF pulses of the desired frequency, phase and pulse amplitude waveform. The generated RF pulses may be applied to the whole body RF coil 34 or to one or more local coils or coil arrays.

The RF system 26 also includes one or more RF receiver channels which may be connected to a corresponding plurality of local coils or to a corresponding plurality of coil elements in a coil array. Each RF receiver channel includes an RF amplifier that amplifies the NMR signal received by the coil to which it is connected and a quadrature detector which detects and digitizes the I and Q quadrature components of the received NMR signal. The magnitude of the received NMR signal may thus be determined at any sampled point by the square root of the sum of the squares of the I and Q components:

$$M=\sqrt{I^2-Q^2},$$

and the phase of the received NMR signal may also be determined:

$$\phi=\tan^{-1}Q/I.$$

The pulse sequence server 118 also optionally receives patient data from a physiological acquisition controller 36. The controller 36 receives signals from a number of different sensors connected to the patient, such as ECG signals from electrodes or respiratory signals from a bellows. Such signals are typically used by the pulse sequence server 118 to synchronize, or "gate", the performance of the scan with the subject's respiration or heart beat.

The pulse sequence server 118 also connects to a scan room interface circuit 38 which receives signals from various sensors associated with the condition of the patient and the magnet system. It is also through the scan room interface circuit 38 that a patient positioning system 40 receives commands to move the patient to desired positions during the scan.

It should be apparent that the pulse sequence server 118 performs real-time control of MRI system elements during a scan. As a result, it is necessary that its hardware elements be operated with program instructions that are executed in a timely manner by run-time programs. The description components for a scan prescription are downloaded from the workstation 110 in the form of objects. The pulse sequence server 118 contains programs which receive these objects and converts them to objects that are employed by the run-time programs.

The digitized NMR signal samples produced by the RF system 26 are received by the data acquisition server 120. The data acquisition server 120 operates in response to description components downloaded from the workstation 110 to receive the real-time NMR data and provide buffer storage such that no data is lost by data overrun. In some scans the data acquisition server 120 does little more than pass the acquired NMR data to the data processor server 122. However, in scans which require information derived from acquired NMR data to control the further performance of the scan, the data acquisition server 120 is programmed to produce such information and convey it to the pulse sequence server 118. For example, during prescans NMR data is acquired and used to calibrate the pulse sequence performed by the pulse sequence server 118. Also, navigator signals may be acquired during a scan and used to adjust RF or gradient system operating parameters or to control the view order in which k-space is sampled. And, the data acquisition server 120 may be employed to process NMR signals used to detect the arrival of contrast agent in an MRA scan. In all these examples the data acquisition server 120 acquires NMR data and processes it in real-time to produce information which is used to control the scan.

The data processing server 122 receives NMR data from the data acquisition server 120 and processes it in accordance with description components downloaded from the workstation 110. Such processing may include, for example: Fourier transformation of raw k-space NMR data to produce two or three-dimensional images; the application of filters to a reconstructed image; the performance of a backprojection image reconstruction of acquired NMR data; the calculation of functional MR images; the calculation of motion or flow images, etc.

Images reconstructed by the data processing server 122 are conveyed back to the workstation 110 where they are stored. Real-time images are stored in a data base memory cache (not shown) from which they may be output to operator display 112 or a display 42 which is located near the magnet assembly 30 for use by attending physicians. Batch mode images or selected real time images are stored in a host database on disc storage 44. When such images have been reconstructed and transferred to storage, the data processing server 122 notifies the data store server 23 on the workstation 110. The workstation 110 may be used by an operator to archive the images, produce films, or send the images via a network to other facilities.

Figure 7:
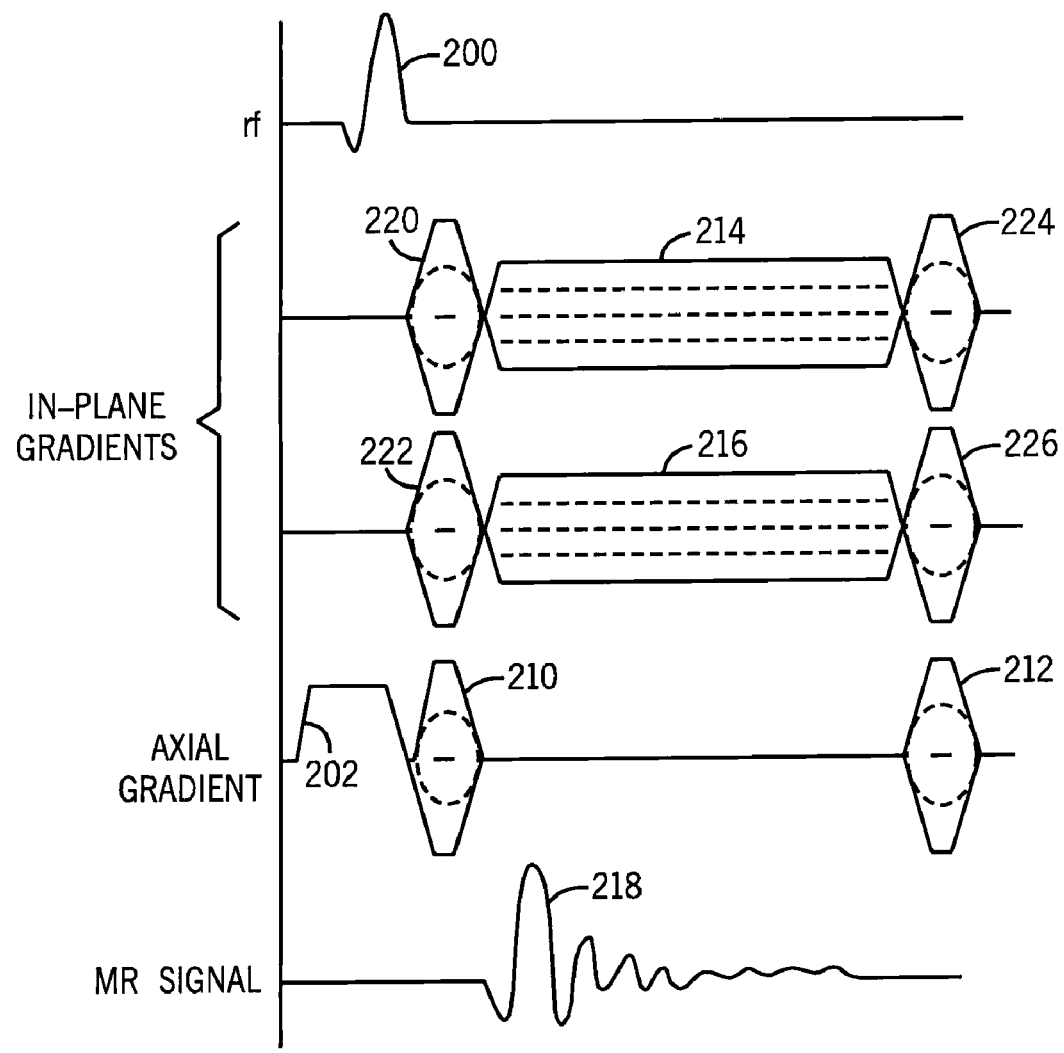
FIG. 7 is a graphic illustration of a hybrid PR pulse sequence performed by the MRI system of FIG. 1 when practicing the preferred embodiment of the present invention.

To practice the preferred embodiment of the invention NMR data is acquired using a projection reconstruction, or radial, pulse sequence such as that shown in FIG. 7. This is a fast gradient-recalled echo pulse sequence in which a selective, asymmetrically truncated sinc rf excitation pulse 200 is produced in the presence of a slice-select gradient 202. The flip angle of the rf pulse 200 is set near the Ernst angle for $T_1$, shortened blood which is typically 30° to 40°.

Figure 8:
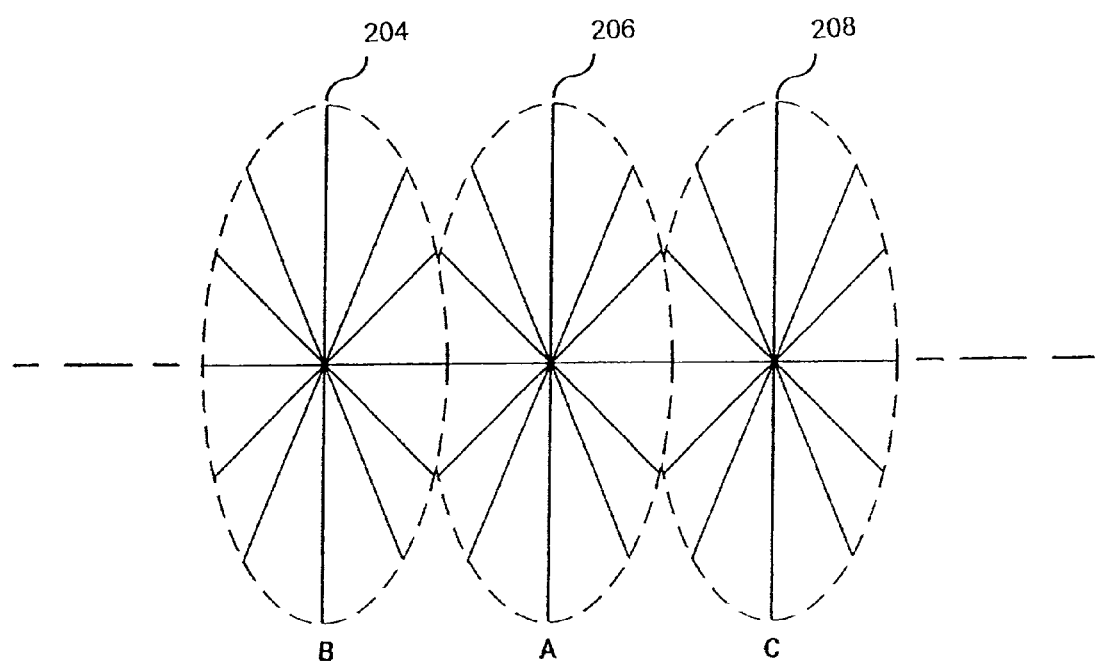
FIG. 8 is a pictorial representation of k-space sampling using the hybrid pulse sequence of FIG. 5.

As will be explained in more detail below, this pulse sequence may be used to acquire a single 2D slice by sampling in a single k-space circular plane, or it may be used to sample a plurality of circular k-space planes as shown at 204, 206 and 208 in FIG. 8. When multiple 2D slices are acquired the axial gradient 202 is a slab select gradient followed by a phase encoding gradient lobe 210 and a rewinder gradient lobe 212 of opposite polarity. This axial phase encoding gradient 210 is stepped through values during the scan to sample from each of the 2D k-space planes 204, 206 and 208.

Two in-plane readout gradients 214 and 216 are played out during the acquisition of an NMR echo signal 218 to sample k-space in a 2D plane 204, 206 or 208 along a radial trajectory. These in-plane gradients 214 and 216 are perpendicular to the axial gradient and they are perpendicular to each other. During a scan they are stepped through a series of values to rotate the view angle of the radial sampling trajectory as will be described in more detail below. Each of the in-plane readout gradients is preceded by a prephasing gradient lobe 220 and 222 and followed by a rewinder gradient lobe 224 and 226.

It should be apparent to those skilled in the art that sampling trajectories other than the preferred straight line trajectory extending from one point on the k-space peripheral boundary, through the center of k-space to an opposite point on the k-space peripheral boundary may be used. One variation is to acquire a partial NMR echo signal 218 which samples along a trajectory that does not extend across the entire extent of the sampled k-space volume. Another variation which is equivalent to the straight line projection reconstruction pulse sequence is to sample along a curved path rather than a straight line. Such pulse sequences are described, for example, in "Fast Three Dimensional Sodium Imaging", MRM, 37:706-715, 1997 by F. E. Boada, et al. and in "Rapid 3D PC-MRA Using Spiral Projection Imaging", Proc. Intl. Soc. Magn. Reson. Med. 13 (2005) by K. V. Koladia et al and "Spiral Projection Imaging: a new fast 3D trajectory", Proc. Intl. Soc. Mag. Reson. Med. 13 (2005) by J. G. Pipe and Koladia. It should also be apparent that the present invention may be employed with 3D as well as 2D versions of these sampling methods and references to the term "pixel" as used hereinafter is intended to refer to a location in either a 2D or a 3D image.

Figure 9:
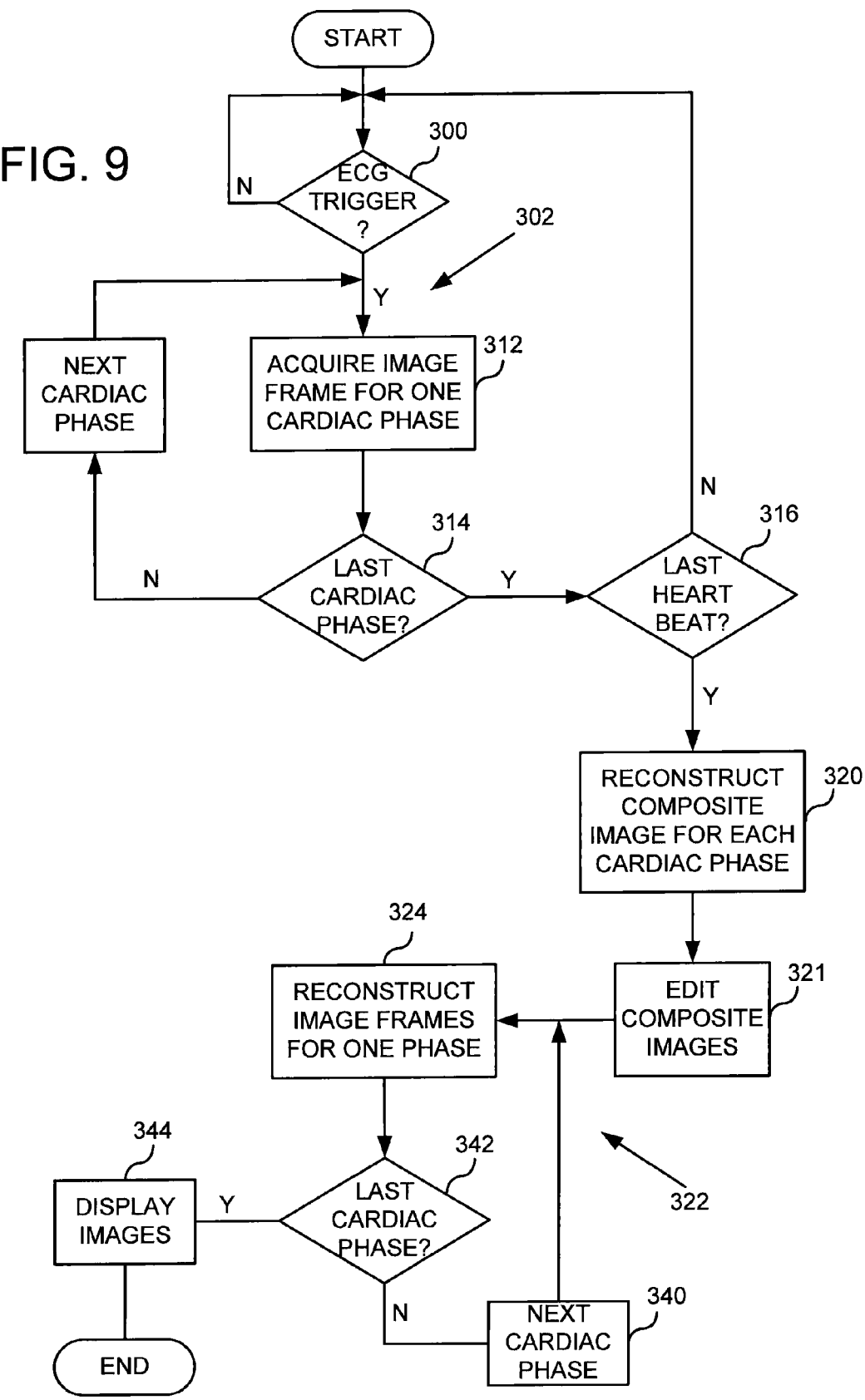
FIG. 9 is a flow chart of the steps in a preferred embodiment of the present invention.
Figure 10:
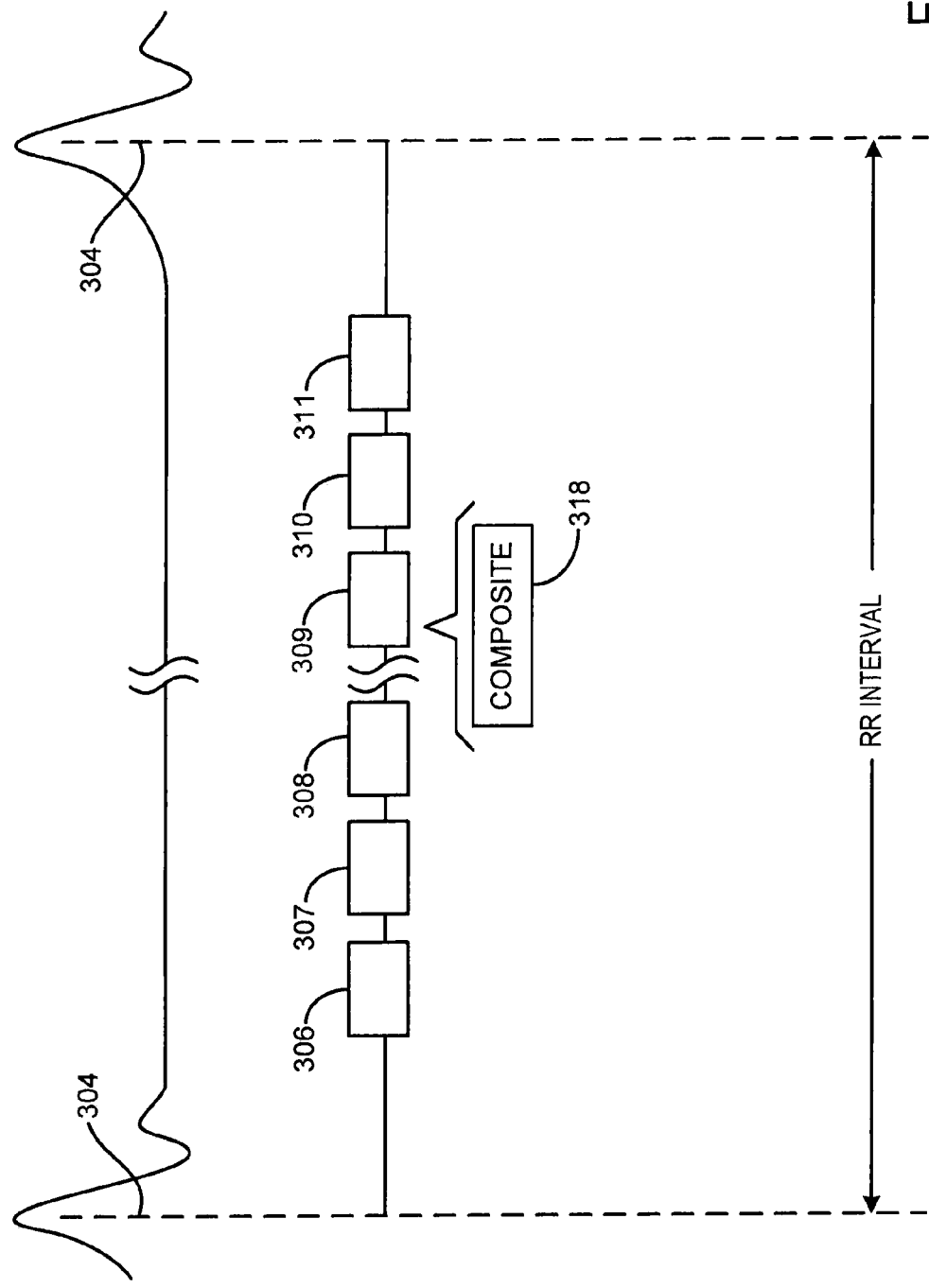
FIG. 10 is pictorial representation of the cardiac gated acquisition of data during one heart beat.

The above-described pulse sequence is employed by the MRI system of FIG. 1 to acquire a series of cardiac gated frame images. In the first preferred embodiment only a single 2D slice is acquired in each image frame. Referring to FIGS. 1 and 9, after the subject is positioned in the bore of the MRI system and the ECG signals are coupled to the physiological acquisition controller 36 the system waits for an ECG trigger signal as indicated at decision block 300. When the trigger signal is received a set of image frames are acquired as indicated generally at 302. This is illustrated pictorially in FIG. 10 where the cardiac cycle is initiated by an ECG trigger signal at 304 and a set of six image frames 306-311 are acquired at predetermined times, or "cardiac phases" during the subsequent RR interval. In the preferred embodiment each image frame acquisition at process block 312 is comprised of 10 projection views which are set to view angles that sample two-dimensional k-space as uniformly as possible. This is a highly undersampled data set and absent the present invention it would result in a very poor quality image if one were to perform a typical image reconstruction.

Figure 11:
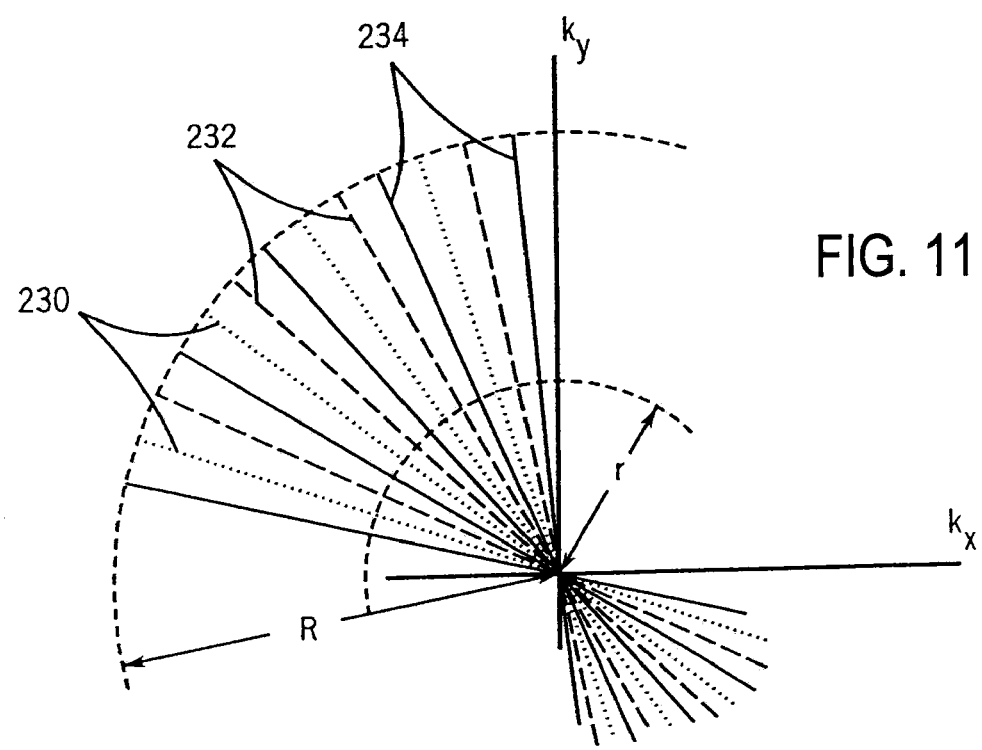
FIG. 11 is a pictorial representation of interleaved sampling of k-space with radial sampling trajectories.

When the last image frame is acquired during the RR interval as determined at decision block 314, the system loops back and awaits the next ECG trigger signal at decision block 300. A similar set of image frames are acquired during the next RR interval except each of the 10 views acquired for each image frame 306-311 during subsequent RR intervals are interleaved with the previously acquired views. This is illustrated in FIG. 11 where projection views indicated by dotted lines 230 are acquired during one RR interval, projection views indicated by dashed lines 232 are acquired during another RR interval, and projection views indicated by solid lines 234 are acquired in yet another RR interval. During a typical breath-hold, from 16 to 20 sets of such interleaved projection views may be acquired.

As indicated above, the views in each acquired image frame are arranged to sample k-space as uniformly as possible and will satisfy the Nyquist sampling criteria out to a radius r as shown in FIG. 11. The combined, interleaved projections 230, 232 and 234 also sample k-space as uniformly as possible, but they more densely sample k-space and satisfy the Nyquist sampling criteria out to a much larger radius R. As a result, when data has been acquired for all the heart beats in a breath-hold as detected at decision block 316 in FIG. 9, a substantial number of interleaved and evenly distributed views have been acquired for each cardiac phase in a composite data set indicated at 318 in FIG. 10.

Referring still to FIG. 9, a composite image is reconstructed for each cardiac phase as indicated at process block 320 using the composite data set 318. In a typical breath-hold of 16 to 20 heartbeats the composite data set will contain from 16 to 20 times the data contained in a single image frame and an image reasonably free of artifacts can be reconstructed using a conventional filtered back projection technique. The resulting composite image may also be edited or filtered as indicated at process block 321 to remove unwanted structures. This can be done manually by displaying the composite images and deleting unwanted structures or automatically by filtering out detectable structures or tissues.

A series of image frames may now be reconstructed for each cardiac phase as indicated at process block 324. The reconstruction of one image frame will now be described and it is an important aspect of the present invention that the composite image for a cardiac phase be used to reconstruct the frame images for that cardiac phase.

Figure 5:
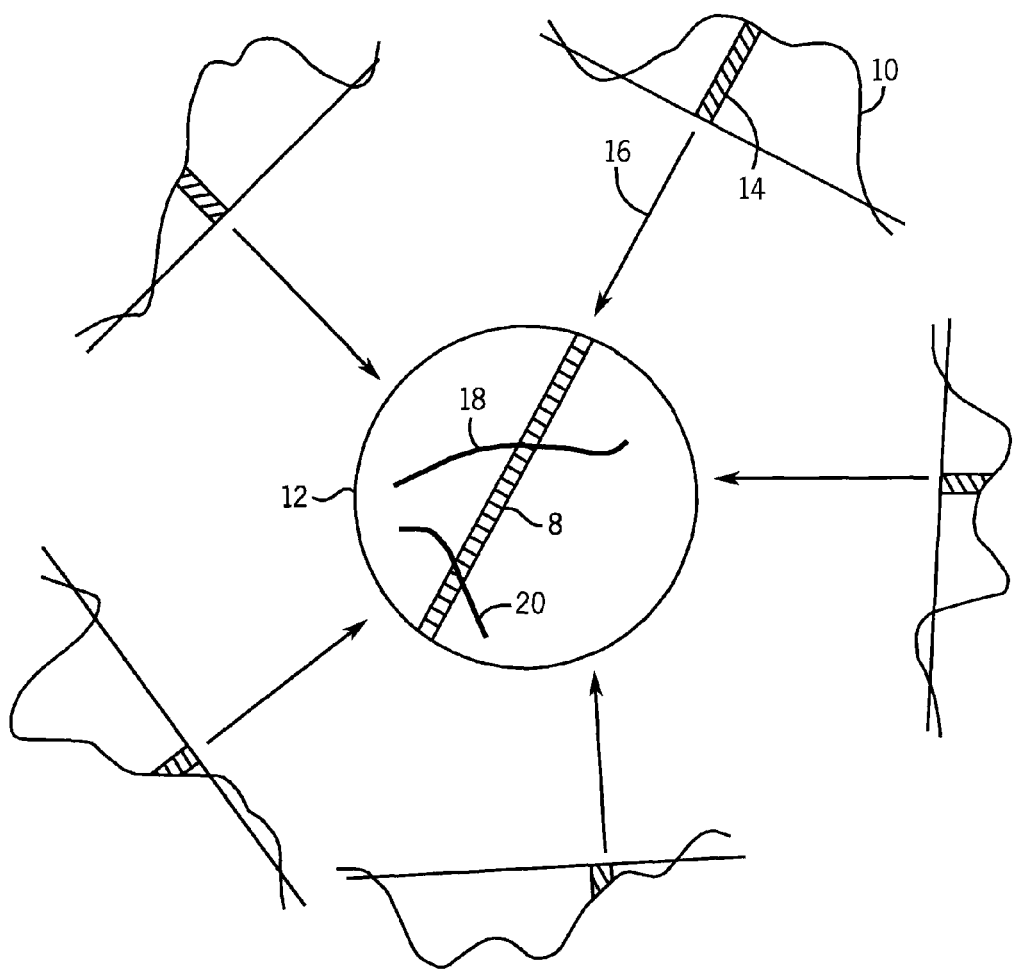
FIG. 5 is a pictorial representation of the backprojection method according to the present invention for a 2D PR image reconstruction.
Figure 6:
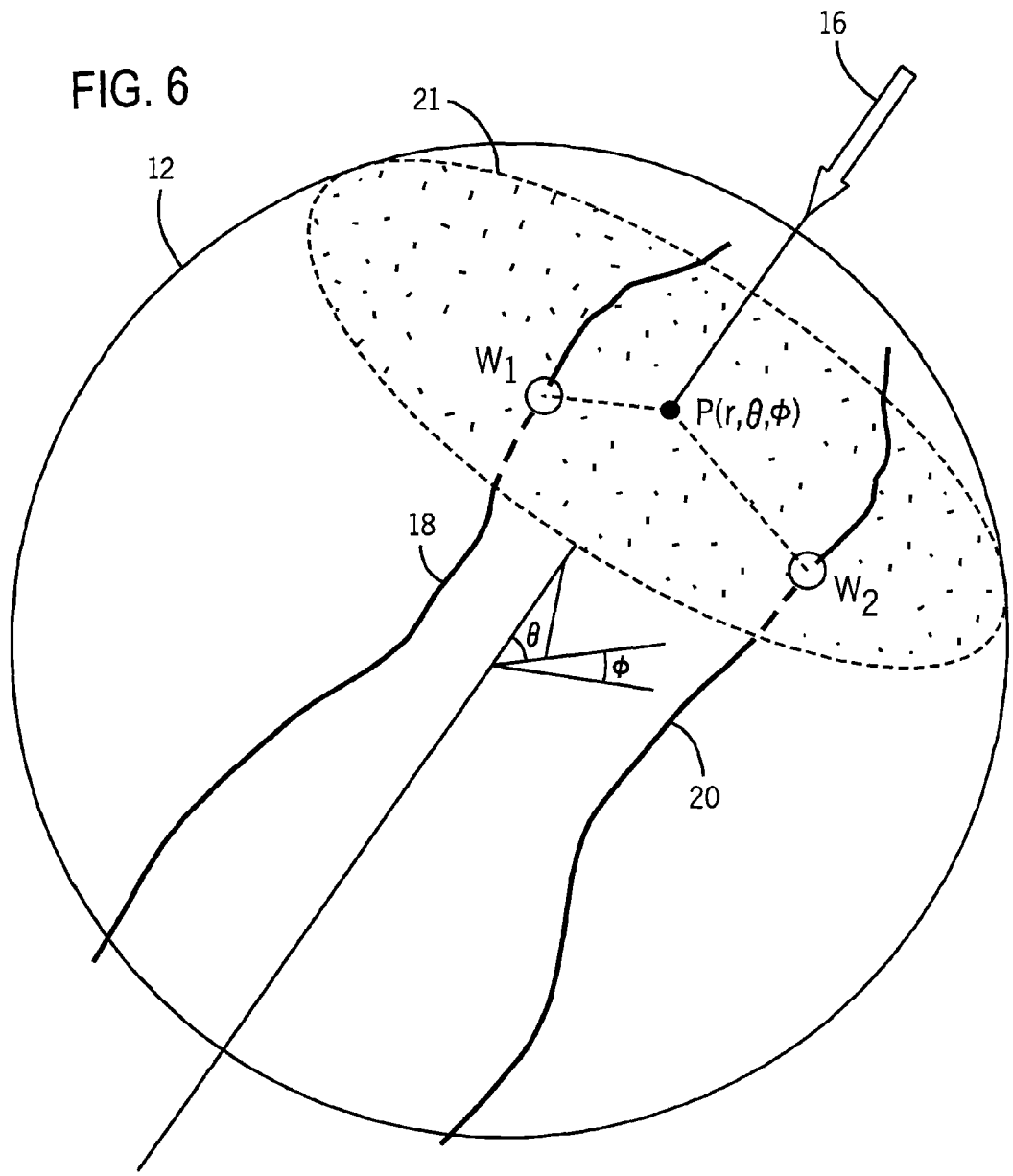
FIG. 6 is a pictorial representation of the backprojection method for a 3DPR image reconstruction.
Figure 12:
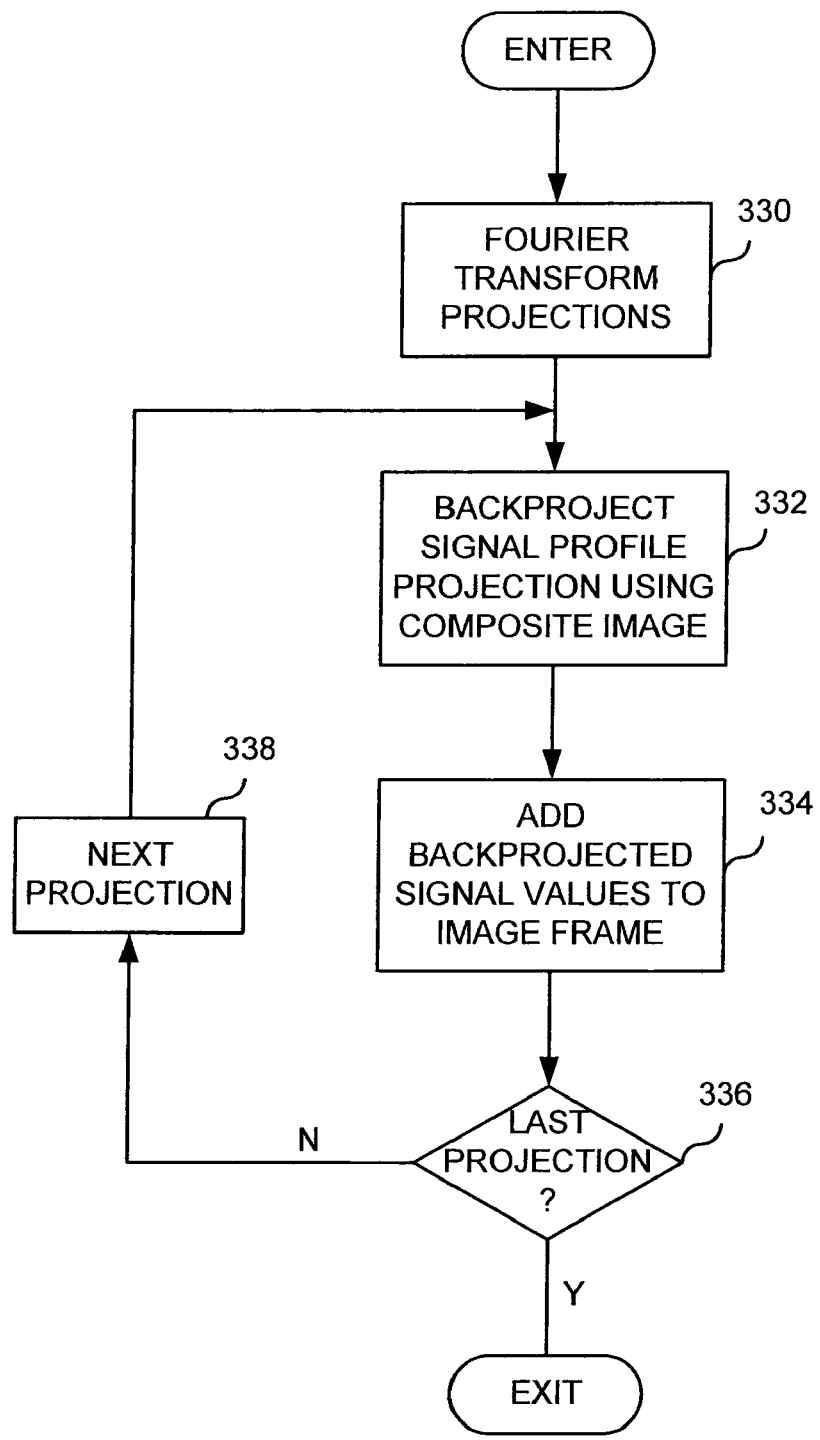
FIG. 12 is a flow chart of the steps for reconstructing a 2D image frame according to the present invention.

Referring particularly to FIG. 12, the first step is to transform the image frame k-space projections (10 in the preferred embodiment) to radon space by Fourier transforming them as indicated at process block 330. The result is a set of signal profiles 10 as depicted in FIG. 5. As indicated at process block 332, each of these signal profiles is then backprojected into the VOI as depicted by path 8 in FIG. 5. This backprojection is weighted by the composite image as described above with reference to equation (2). That is, the backprojection value (P) at any pixel (n) is weighted by the magnitude ($C_n$) of the same pixel in the composite image.

As indicated at process block 334, the backprojected signal values ($S_n$) are then added to an image frame that is being reconstructed. The system then loops back at decision block 336 to backproject the next signal profile 10 as indicated at process blocks 338 and 332. The signal values ($S_n$) of all the backprojected signal profiles 10 are, therefore, added to the image frame with a weighting determined by corresponding pixel values in the higher quality composite image. The composite image is higher in quality because it is reconstructed from far more projection views and this results in fewer artifacts. The composite image is also higher quality because the projection views used to reconstruct it are acquired over a much longer time span. Generally, the SNR of an image frame is proportional to the square root of its acquisition duration. It is a discovery of this invention that the higher quality of the composite image is conveyed to the image frame through this unique, highly constrained reconstruction process.

Returning to the flow chart in FIG. 9, the image frames for one cardiac phase are reconstructed with their corresponding composite image and then the image frames for the next cardiac phase are reconstructed as indicated at process block 340. When the image frames for all the cardiac phases have been reconstructed as determined at decision block 342, they may be displayed in a number of ways as indicated at process block 344.

Figure 13:
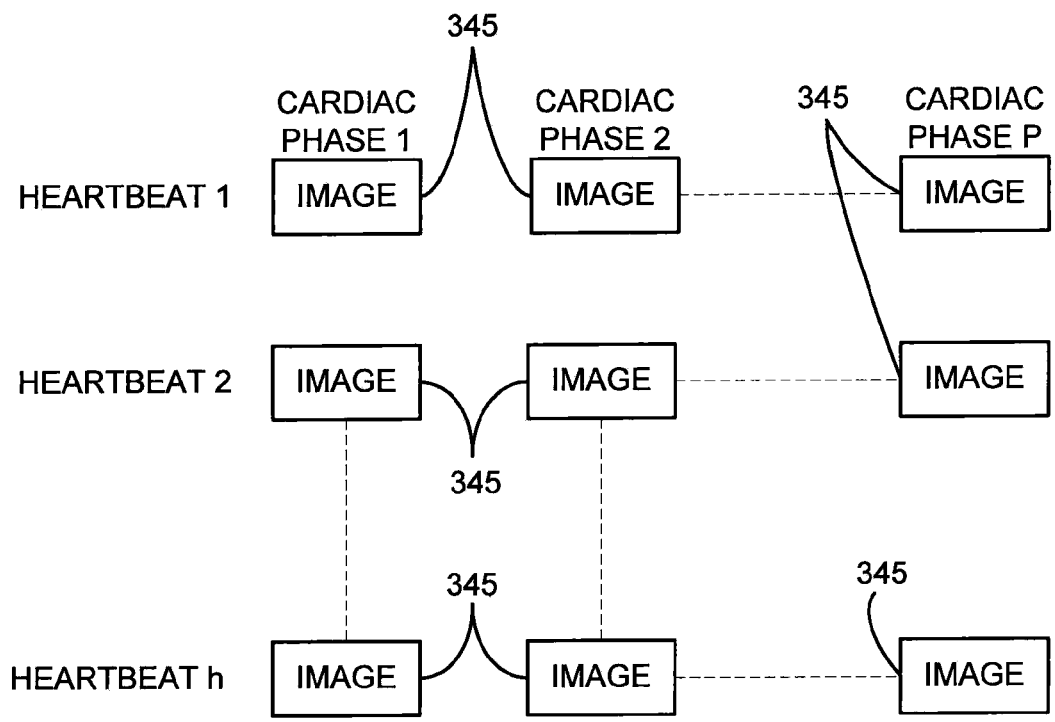
FIG. 13 is a pictorial view of the images produced using the method of FIG. 10.

The above described scan produces a series of image frames at each of a plurality of cardiac phases. This is shown in FIG. 13 where each reconstructed image frame 345 is associated with a particular cardiac phase and a particular heartbeat. These image frames 345 may be displayed in a number of different ways. First, at any selected point in time during the breath-hold (i.e., heartbeat) the images that depict the subject at successive cardiac phases can be displayed. If the subject is the human heart, for example, the successive cardiac phase images will show the structure of the heart as it changes throughout one heart beat.

The images 345 at any particular cardiac phase can also be viewed over a succession of heart beats. In this case the cardiac motion is frozen and one sees how the structures change over time. This display mode is particularly useful when a contrast agent is employed and the series of images 345 depict the inflow of contrast agent into the field of view. Such a contrast enhanced embodiment of the invention will now be described.

Figure 14:
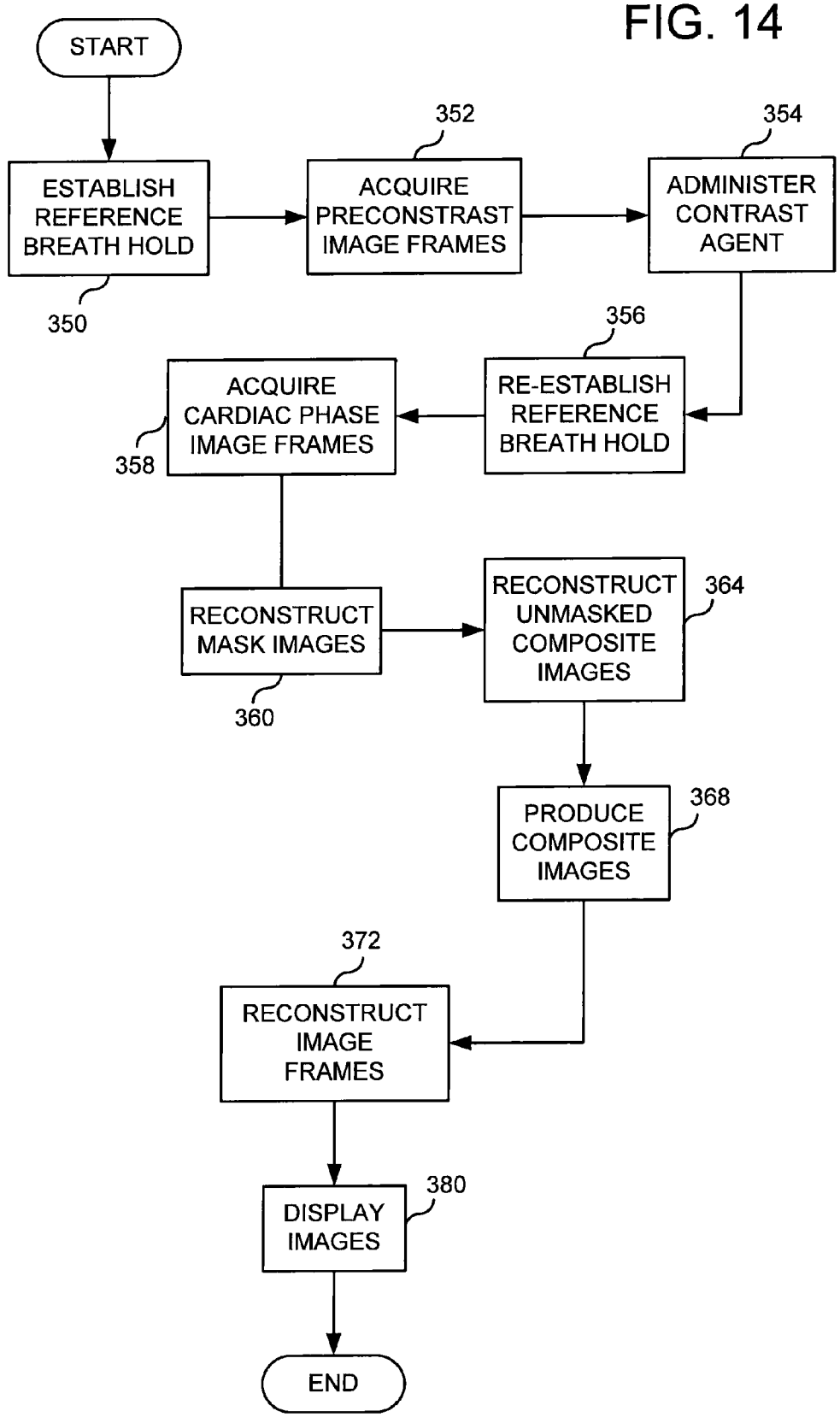
FIG. 14 is a flow chart of the steps in a second, contrast enhanced embodiment of the invention.

A preferred method for employing a contrast agent in an ECG gated scan is depicted in FIG. 14. This particular embodiment employs two breath-holds and the first step is to direct the patient to establish a first, reference breath-hold as indicated at process block 350. This may be done using a monitor device such as that disclosed in U.S. Pat. No. 5,363,844 entitled "Breath-hold Monitor For MR Imaging" which provides visual feedback to the patient regarding respiratory motion. As indicated at process block 352, a series of cardiac phase image frames are then acquired as described above during this initial breath-hold.

A contrast agent is then administered as indicated at process block 354 and a second breath-hold is re-established at the reference position as indicated at process block 356. Using the above described breath-hold monitor, for example, the patient inhales and then exhales until the feedback lights on the monitor indicate that the reference position has been reached. As indicated at process block 358, another set of cardiac phase image frames are acquired during this second breath-hold as the contrast agent flows into the field of view.

Figure 15:
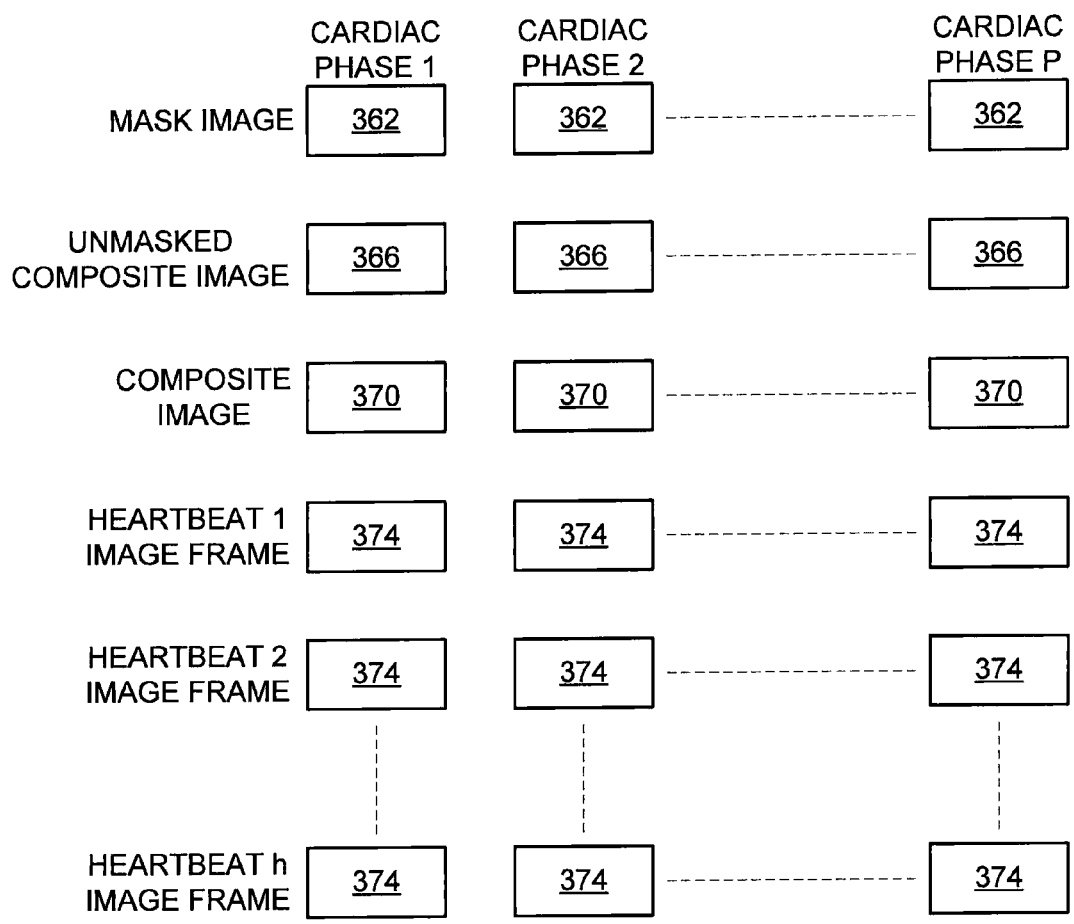
FIG. 15 is a pictorial representation of the images produced using the method of FIG. 14.

As indicated at process block 360, a pre-contrast mask image is produced for each cardiac phase. This is done by combining all the projections acquired throughout the first breath-hold at each cardiac phase and performing a conventional filtered backprojection image reconstruction with the combined projections. For example, if 20 heartbeats occur during this first breath-hold and 10 interleaved projection views are acquired during each cardiac phase, then a total of 10×20=200 projection views are used to reconstruct each mask image. A mask image 362 is thus produced for each cardiac phase as illustrated in FIG. 15.

As indicated by process block 364, an unmasked composite image is reconstructed next for each cardiac phase. This is done by combining all the interleaved projections acquired throughout the second, post contrast breath-hold at each cardiac phase and performing a conventional filtered backprojection image reconstruction with the combined (e.g., 200) interleaved projections. An unmasked composite image 366 is thus produced for each cardiac phase as illustrated in FIG. 15.

A final composite image is now produced for each cardiac phase as indicated at process block 368. This is done by subtracting the mask image 362 for each cardiac phase from its corresponding unmasked composite image 366. As illustrated in FIG. 15, a composite image 370 is thus produced for each cardiac phase. The masked composite image 370 indicates those image pixels which have changed in intensity due to the arrival of contrast agent, which may be arteries in an MRA study or the chambers of the heart in a cardiac study. It should be apparent that the same masked composite image 370 can also be produced by subtracting the pre-contrast projection views from the corresponding post-contrast projection views and reconstructing the masked composite image 370 from the difference projection views.

A set of image frames can now be reconstructed for each cardiac phase as indicated at process block 372. This is done as described above and shown in FIG. 12 using the masked composite image 370 for the cardiac phase and the projections acquired during each heartbeat for that cardiac phase. To produce the desired sparse data set for this highly constrained backprojection reconstruction, the corresponding mask projection views are subtracted from projection views used to reconstruct this image frame. As shown in FIG. 15 an image frame 374 is thus reconstructed for each heart beat and for each cardiac phase. These can be displayed in a number of different ways as discussed above and indicated at process block 380.

Another preferred embodiment of the invention employs the multi-slice capability of the hybrid PR pulse sequence in FIG. 7 to acquire multi-slice image frames during each heart beat and at each cardiac phase. Multiple, contiguous slices provide a 3D volume from which maximum intensity projection (MIP) images can be produced. This is important when structures are being imaged that do not lie entirely in one 2D plane. This multislice embodiment may be employed in the contrast enhanced acquisition described above with reference to FIG. 14, but a multislice embodiment without contrast enhancement will now be described with reference to FIG. 16. This embodiment is similar in many ways to the embodiment described above with reference to FIG. 10 and steps that are essentially the same have been identified with the same reference numbers in FIG. 16.

Figure 16:
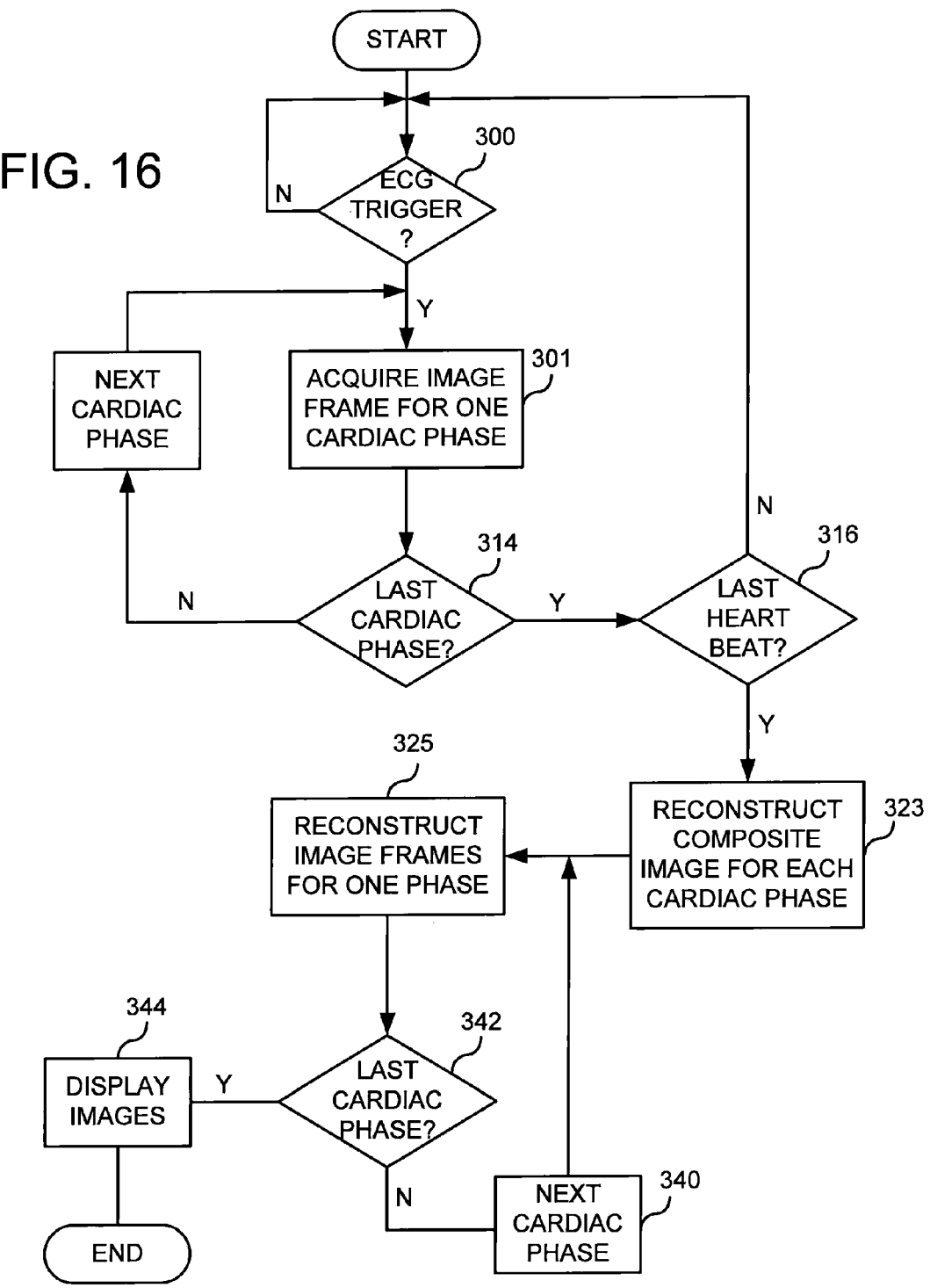
FIG. 16 is a flow chart of the steps in another preferred embodiment of the invention.
Figure 17:
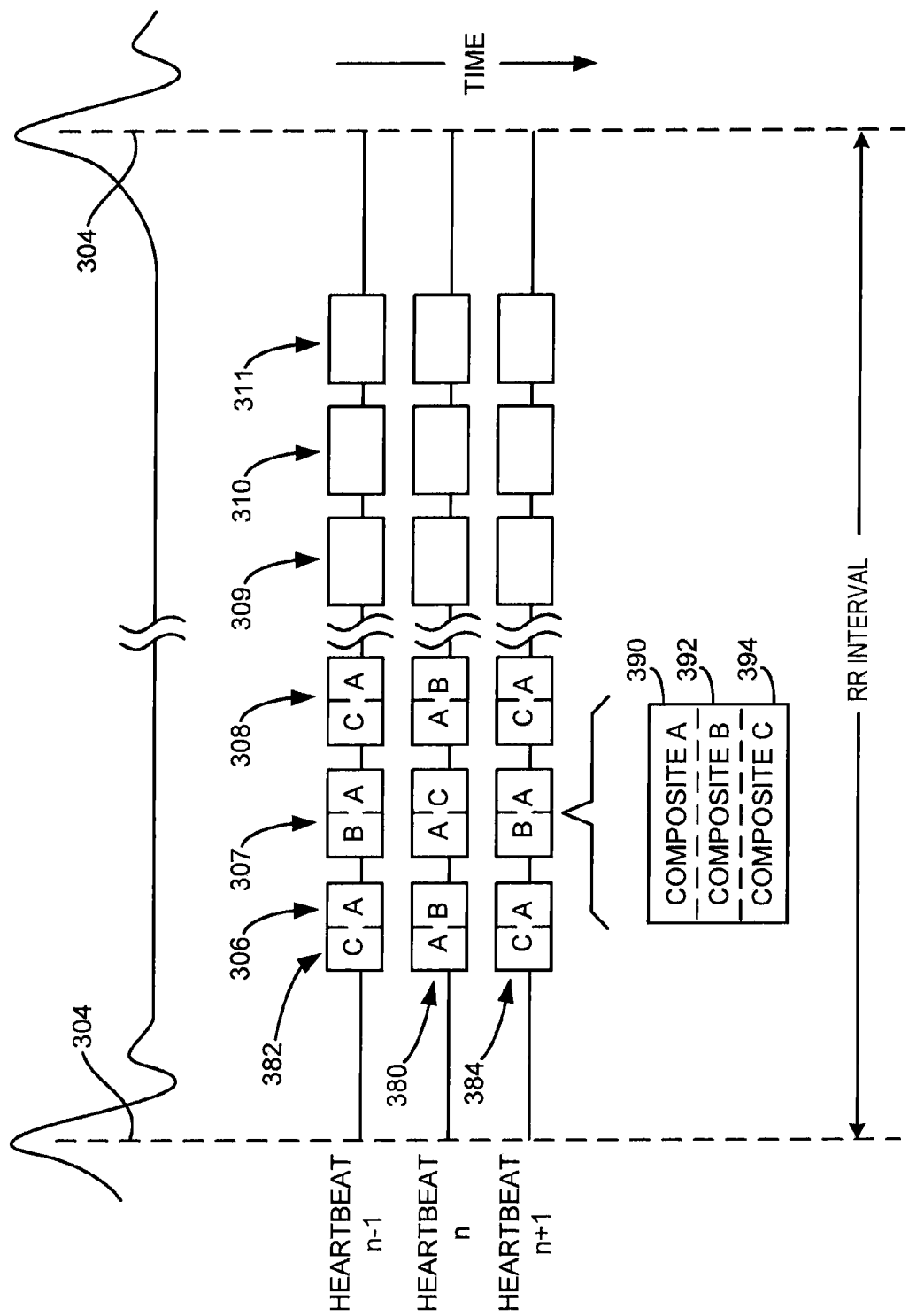
FIG. 17 is a pictorial representation of the cardiac gated acquisition of data during one heartbeat when practicing the method of FIG. 16.

Referring particularly to FIGS. 16 and 17, a cardiac triggered scan is conducted in which a series of image frames are acquired at a plurality of cardiac phases during each heartbeat throughout a breath-hold. During each heart beat a series of image frames 306-311 are acquired at process block 301 similar to that described above. However, instead of acquiring a single set of 10 projection views that sample a single k-space slice, two sets of 10 projection views are acquired during each cardiac phase. Each set of 10 projection views is phase encoded differently along the axial gradient (FIG. 7) such that two adjacent 2D slices of k-space are sampled. As will now be described, an image frame comprised of three 2D slices is ultimately formed at each cardiac phase. Referring to FIG. 8, these include a central k-space slice 206 that will be referred to below as "A" and two peripheral k-space slices 204 and 208 referred to below as "B" and "C". However, to reduce the scan time required to acquire each image frame, only two of these three slices are acquired during any single cardiac phase.

As shown best in FIG. 17, during each acquisition of a frame image at a particular cardiac phase, the central slice A is acquired along with one of the peripheral slices B or C. The sampling pattern is such that at any cardiac phase the central slice A is acquired, one of the peripheral slices B or C is acquired, and the other peripheral slice can be produced from temporally adjacent acquisitions. For example, in FIG. 17 the first cardiac phase image frame 380 acquired during the $n^{th}$ heartbeat of a breath-hold acquires the A and B slices during twenty repetitions of the pulse sequence of FIG. 7. During the same cardiac phase of the n−1 and n+1 heartbeats the A and C slices are acquired at 382 and 384. When reconstructing the image frame for the first cardiac phase of the $n^{th}$ heartbeat, therefore, slice C data is calculated by interpolating between the temporally adjacent C slices acquired at 382 and 384 during the n−1 and n+1 heartbeats.

Referring again to FIG. 16, after all the image frames for all the heartbeats in a breath-hold have been acquired as determined at decision block 316, a set of composite images are reconstructed from the acquired data as indicated at process block 323. First, a one-dimensional fast Fourier transformation is performed along the axial, phase encoding axis of the acquired k-space data sets. The resulting hybrid space data sets are each comprised of three axial slices (A, B and C) of projection views as shown in FIG. 8. Three composite images are reconstructed for each cardiac phase, one for each slice A, B and C. More specifically, for each cardiac phase the slice A projections acquired during the entire breath-hold are combined as shown in FIG. 17 for the second cardiac phase to form a composite A data set 390, the slice B projections are combined to form a composite B data set 392, and the slice C projections are combined to form a composite C data set 394. The projections that are combined to form the composite data sets 390, 392 and 394 are interleaved as described above with reference to FIG. 11 and they thus sample the k-space slices A, B and C substantially uniformly. Importantly, the composite data sets 390, 392 and 394 sample the slices A, B and C far more densely than any of the acquired image frames during the cardiac phase. As a result, composite images may be reconstructed from the composite data sets 390, 392 and 394 formed for each cardiac phase using a conventional image reconstruction method. Each of the three slices is separately reconstructed using a conventional two-dimensional image reconstruction method. This may be a filtered backprojection or a regridding of the 2D projections in each slice followed by a two-dimensional fast Fourier transformation.

Following reconstruction of the composite images the image frames for each cardiac phase are reconstructed as indicated at process block 325. As with the previous embodiments described above, this image reconstruction employs the highly constrained backprojection method and the composite images to enhance the SNR and reduce image artifacts in the highly undersampled image frames.

The reconstruction of each image frame can be done in a number of different ways. First, the limited set of A, B and C phase encoded projection views for a cardiac phase may be Fourier transformed along the axial, phase encoding gradient axis to form three slices. Each of the three resulting slices is comprised of a limited set of projection views and a slice image is reconstructed therefrom using the above-described method illustrated in FIG. 12. That is, each projection view is Fourier transformed to Radon space and then it is backprojected using the composite image for that slice to weight each backprojected value. Three contiguous image frame slices are thus reconstructed for each cardiac phase during each heartbeat and these may be displayed as a three-dimensional image. Also, a maximum intensity pixel projection (MIP) image may be produced from the three-dimensional image.

In the above-described reconstruction method the Fourier transformation along the axial, phase encoding gradient axis was done first. This is preferred when A, B and C phase encoded projection views in the image frame being reconstructed are not interleaved with each other. If they are interleaved, then an alternative method is preferred in which the respective A, B and C phase encoded projection views are separately backprojected using the highly constrained backprojection method and composite image weighting as described above before performing the Fourier transformation along the gradient axis. The resulting data set is then regridded to align the samples along the axial, phase encoding axis. Then the Fourier transformation along the axial, phase encoding gradient axis is performed on the resulting regridded, hybrid data set.

Rather than converting the image reconstruction process to that of three, 2D slices, a three-dimensional reconstruction of the A, B and C phase encoded data sets at each cardiac phase may be performed directly. A number of methods to do this are described in co-pending U.S. patent application Ser. No. 11/482,372 filed on Jul. 7, 2006 and entitled "HIGHLY CONSTRAINED IMAGE RECONSTRUCTION METHOD". These methods are incorporated herein by reference.

The invention claimed is:

1. A method for producing an image of a subject positioned in a field of view (FOV) of a magnetic resonance imaging (MRI) system, the steps comprising:
   a) acquiring with the MRI system a set of projection views at each of a plurality of cardiac phases and during each of a plurality of heartbeats;
   b) producing a composite image for each cardiac phase with projection views acquired during the corresponding cardiac phase for a plurality of heartbeats, each composite image depicting the subject at the corresponding cardiac phase;
   c) reconstructing an image of the subject at a selected cardiac phase by:
      c)i) backprojecting a set of projection views acquired at the selected cardiac phase into the FOV and weighting the value backprojected into each image pixel by the value of the corresponding pixel in the composite image that depicts the subject during the selected cardiac phase; and
      c)ii) summing the backprojected values for each image pixel.

2. The method as recited in claim 1 in which the projection views acquired at each cardiac phase are interleaved.

3. The method as recited in claim 1 in which each image pixel backprojected value Sn is calculated in step c)i) as $$S_n = (P \times C_n) \Big/ \sum_{n=1}^{N} C_n$$

where:
P=the projection view value being backprojected;
$C_n$=corresponding pixel value in the composite image;
$S_n$=the value of the nth pixel along the backprojecting path; and
N=total number of pixels along the backprojection path.

4. The method as recited in claim 1 in which step b) includes editing the composite image to remove an object therein and to thereby substantially minimize the appearance of that object in the reconstructed image.

5. The method as recited in claim 1 in which step c) includes Fourier transforming each projection view prior to backprojecting the view.

6. The method as recited in claim 1 in which step c) is repeated to produce an image at each of a plurality of cardiac phases in each of a plurality of heartbeats.

7. The method as recited in claim 1 in which step a) is performed under the direction of a hybrid 2D PR pulse sequence that acquires a plurality of sets of projection views at each cardiac phase that depict a corresponding plurality of slices of the subject.

8. The method as recited in claim 7 in which step b) includes producing a composite image for each slice at each cardiac phase.

9. The method as recited in claim 8 in which step c) includes reconstructing an image of the subject at each slice during the selected cardiac phase using the composite images corresponding to the selected cardiac phase and slice.

10. The method as recited in claim 9 in which the number of slice images reconstructed at the selected cardiac phase in step c) is greater than the number of sets of projection views acquired at each cardiac phase using the hybrid 2D PR pulse sequence.

11. The method as recited in claim 10 which includes producing an additional set of projection views at the selected cardiac phase using projection views other than the set of projection views backprojected in step c) during the selected cardiac phase.

12. The method as recited in claim 11 in which the additional set of projection views are calculated by interpolating between sets of projection views acquired at the same cardiac phase but during both the heartbeat previous to and following the heartbeat of the selected cardiac phase.

13. The method as recited in claim 1 wherein:
step a) includes:
   a)i) acquiring a set of precontrast projection views with the MRI system at a selected cardiac phase following a gating signal and at each of a plurality of heartbeats;
   a)ii) administering a contrast agent;
   a)iii) acquiring a set of post-contrast projection views with the MRI system at the selected cardiac phase following a gating signal and at each of a plurality of heartbeats;
step b) includes:
   b)i) subtracting the precontrast projection views from the corresponding post-contrast projection views;
   b)ii) producing a composite image from substantially all the subtracted projection views acquired at the selected cardiac phase; and step c) includes backprojecting the subtracted projection views acquired at the selected cardiac phase and weighting the value backprojected by a corresponding value in the composite image.

14. A method for producing an image of a subject positioned in a field of view (FOV) of a magnetic resonance imaging (MRI) system, the steps comprising:
   a) acquiring with the MRI system a plurality of views of the subject at each of a plurality of cardiac phases during each of a plurality of heartbeats;
   b) reconstructing a composite image using views acquired in step a) from a plurality of heartbeats and at a selected cardiac phase, the composite image having a value at each composite image pixel that is indicative of the subject at that pixel location in the FOV at the selected cardiac phase; and
   c) reconstructing an image of the subject by:
      c)i) producing an image data set from views acquired in step a) at the selected cardiac phase; and
      c)ii) producing an image of the subject using the image data set and a highly constrained backprojection method which weights each backprojected image pixel by the corresponding pixel value in the composite image.

15. The method as recited in claim 14 in which step a) includes acquiring a plurality of phase encoded projection views at each of the plurality of cardiac phases, step b) includes reconstructing a composite image for each phase encoding at the selected cardiac phase; and the composite images are used in step c) to reconstruct said image of the subject.

16. The method as recited in claim 14 in which the views acquired at the selected cardiac phase in step a) are projection views acquired at interleaved projection angles during successive heartbeats, the image data set produced in step c)i) includes selecting a set of said projection views, and the composite image is reconstructed in step b) from substantially all of the interleaved projection views.

17. The method as recited in claim 14 in which the views are acquired in step a) at a plurality of selected cardiac phases, a corresponding plurality of composite images are reconstructed therefrom in step b), and a plurality of images are reconstructed in step c) at a corresponding plurality of cardiac phases.

18. The method as recited in claim 14 in which a plurality of images are produced in step c) from views acquired during a corresponding plurality of heartbeats at the selected cardiac phase.

19. The method as recited in claim 14 in which step c)ii) includes normalizing each image pixel.

20. A method for producing a contrast enhanced, cardiac gated image with a magnetic resonance imaging (MRI) system, the steps comprising:
   a) acquiring a set of views with the MRI system at a selected cardiac phase following a gating signal and at each of a plurality of heartbeats;
   b) reconstructing a mask image from substantially all the views acquired at the selected cardiac phase;
   c) administering a contrast agent;
   d) acquiring a set of post-contrast views with the MRI system at the selected cardiac phase following a gating signal and at each of a plurality of heartbeats;
   e) reconstructing an unmasked composite image from substantially all the views acquired at the selected cardiac phase;
   f) producing a composite image by subtracting the mask image from the unmasked composite image;
   g) reconstructing a frame image from a set of post-contrast views acquired at the selected cardiac phase during one heartbeat; and
   wherein step g) includes weighting each pixel in the frame image using the composite image.

21. The method as recited in claim 20 in which the views are projection views and step g) is performed using a highly constrained backprojection method which includes backprojecting the post-contrast views acquired at the selected cardiac phase and weighting the value backprojected by a corresponding value in the composite image.

22. The method as recited in claim 20 in which the views acquired in step d) are interleaved.

23. The method as recited in claim 20 in which step g) is repeated to reconstruct a frame image at each of a plurality of heartbeats.

24. The method as recited in claim 20 in which steps d), e), f) and g) are repeated to produce a frame image at another selected cardiac phase.

25. The method as recited in claim 24 in which step g) is repeated to reconstruct a frame image at each of a plurality of heartbeats at each of a plurality of selected cardiac phases.

26. A method for producing a contrast enhanced, cardiac gated image with a magnetic resonance imaging (MRI) system, the steps comprising:
   a) acquiring a set of precontrast projection views with the MRI system at a selected cardiac phase following a gating signal and at each of a plurality of heartbeats;
   b) administering a contrast agent;
   c) acquiring a set of post-contrast projection views with the MRI system at the selected cardiac phase following a gating signal and at each of a plurality of heartbeats;
   d) subtracting the precontrast projection views from the corresponding post-contrast projection views;
   e) producing a composite image from substantially all the subtracted projection views acquired at the selected cardiac phase; and
   f) reconstructing a frame image from a set of subtracted projection views acquired at the selected cardiac phase during one heartbeat, using a highly constrained backprojection method which includes backprojecting the subtracted projection views acquired at the selected cardiac phase and weighting the value backprojected by a corresponding value in the composite image.

27. The method as recited in claim 26 in which the views acquired in step d) are interleaved.

28. The method as recited in claim 26 in which step f) is repeated to reconstruct a frame image at each of a plurality of heartbeats.

29. The method as recited in claim 26 in which steps c), d), e) and f) are repeated to produce a frame image at another selected cardiac phase.

30. The method as recited in claim 29 in which step f) is repeated to reconstruct a frame image at each of a plurality of heartbeats at each of a plurality of selected cardiac phases.

* * * * *

UNITED STATES PATENT AND TRADEMARK OFFICE
CERTIFICATE OF CORRECTION

| | | |
|---|---|---|
| PATENT NO. | : 7,865,227 B2 | Page 1 of 1 |
| APPLICATION NO. | : 11/524750 | |
| DATED | : January 4, 2011 | |
| INVENTOR(S) | : Charles A. Mistretta | |

It is certified that error appears in the above-identified patent and that said Letters Patent is hereby corrected as shown below:

In the Specifications:
Column 1, line 4, please insert the following paragraph after the title of the invention:

-- STATEMENT REGARDING FEDERALLY SPONSORED RESEARCH
   This invention was made with government support under Grant Nos. HL072260 and HL066488 awarded by the National Institute of Health. The government has certain rights in this invention. --

Signed and Sealed this
Twenty-second Day of February, 2011

David J. Kappos
*Director of the United States Patent and Trademark Office*